(12) United States Patent
Fang

(10) Patent No.: US 7,749,723 B2
(45) Date of Patent: Jul. 6, 2010

(54) UNIVERSAL READOUT FOR TARGET IDENTIFICATION USING BIOLOGICAL MICROARRAYS

(75) Inventor: Ye Fang, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 280 days.

(21) Appl. No.: 11/546,266

(22) Filed: Oct. 11, 2006

(65) Prior Publication Data
US 2007/0031884 A1 Feb. 8, 2007

Related U.S. Application Data

(62) Division of application No. 10/392,193, filed on Mar. 19, 2003, now abandoned.

(51) Int. Cl.
*C12Q 1/00* (2006.01)
*G01N 21/00* (2006.01)
*G01N 21/76* (2006.01)
*G01N 33/00* (2006.01)
*G01N 33/53* (2006.01)
*G01N 33/543* (2006.01)
*G01N 33/551* (2006.01)
*C12M 1/34* (2006.01)
*C12M 3/00* (2006.01)

(52) U.S. Cl. .................. 435/7.93; 435/4; 435/7.1; 435/7.95; 435/287.1; 436/518; 436/524; 436/164; 436/172; 436/807

(58) Field of Classification Search .................. None
See application file for complete search history.

(56) References Cited

U.S. PATENT DOCUMENTS

| 5,439,829 | A | * | 8/1995 | Anderson et al. ........... 436/518 |
| 5,482,867 | A | | 1/1996 | Barrett et al. ............... 436/518 |
| 5,726,147 | A | | 3/1998 | Ruf et al. ........................ 514/2 |
| 5,876,946 | A | | 3/1999 | Burbaum et al. ............. 435/7.1 |
| 6,329,209 | B1 | * | 12/2001 | Wagner et al. ................ 506/13 |
| 6,489,159 | B1 | | 12/2002 | Chenchik et al. ......... 435/287.2 |

FOREIGN PATENT DOCUMENTS

| WO | WO 02/18655 | 3/2002 |
| WO | WO 02/052038 | 7/2002 |

OTHER PUBLICATIONS

Fang et al. Ganglioside microarrays for toxin detection. Langmuir (2003), 19:1500-1505.*
Mathai Mammen et al., "Polyvalent Interactions in Biological Systems: Implications for Design and Use of Multivalent Ligands and Inhibitors", Angew. Chem. Int. Ed. 1998, vol. 37, pp. 2754-2794.
Michael P. Czech, "PIP2 and PIP3: Complex Roles at the Cell Surface", Cell, vol. 100, Mar. 17, 2000, pp. 603-606.

* cited by examiner

*Primary Examiner*—Unsu Jung
*Assistant Examiner*—Leon Y. Lum
(74) *Attorney, Agent, or Firm*—Tina N. Thompson

(57) ABSTRACT

A method and apparatus for implementing the method is provided. The method involves performing an indirect competitive binding assay on a microarray to identify biological or chemical targets and screen for compounds of interest. The microarray comprises a common ligand located among membrane-, lipid- or protein-associated active binding sites. The method takes advantage of known or well-characterized binding kinetics, and steric interference between biological or chemicals targets of interest and universal readout units for different binding sites within the limited confines of a microspot. The biological targets, chemicals or organisms can specifically bind to target-binding sites, while the universal readout unit binds to the ligands in the microspot.

5 Claims, 5 Drawing Sheets

UNIVERSAL READOUT FOR TARGET IDENTIFICATION USING BIOLOGICAL MICROARRAYS

CROSS REFERENCE TO RELATED APPLICATION

This is a divisional of U.S. patent application Ser. No. 10/392,193 filed on Mar. 19, 2003 now abandoned, the content of which is relied upon and incorporated herein by reference in its entirety, and the benefit of priority under 35 U.S.C. §120 is hereby claimed.

FIELD OF THE INVENTION

The present invention relates to a method and apparatus for performing biological assays. In particular, the invention describes the use of indirect competitive binding assays for biological target identification and/or chemical compound screening using two-dimensional biological microarrays.

BACKGROUND

In a given living organism, thousands of genes and their products (i.e., RNA and proteins) function in a complicated and orchestrated way that creates the mystery of life. Traditional methods in molecular biology, biochemistry and cell biology generally work on a "one target (i.e., gene, protein) in one experiment" basis. This means that the throughput is very limited, and it is hard to obtain the "whole picture" of gene function and the "dynamic network" of protein function (i.e., protein-protein, protein-small molecule interaction, signaling pathways).

In the past several years, researches in the field of genomics have endeavored to develop analytical methods to simultaneous, quantitative monitor the expression levels of many thousands of genes in an organism. Similarly in the field of proteomics, the race to develop analytical methods for the simultaneous, quantitative analysis of many proteins with respect to their abundance, locations, modifications, temporal alterations, and interactions with other biological and chemical molecules has increased.

Among the various potential methods, microarray technology has been widely viewed as a revolutionary approach, which enables the simultaneous analysis of potentially thousands of molecular parameters within a single experiment. An array is an orderly arrangement of samples. Development of surface-based assays in which numerous molecules of biological interest are immobilized on a surface in a spatially addressable manner has been an important characteristic of microarray technology. Currently, biological microarrays almost all immobilize many biological molecules on the surface of a solid substrate. Each immobilized molecule is confined in a limited space on the substrate surface (i.e., a microspot with a typical diameter of several hundreds of microns), and each corresponding microspot is arranged in a defined location in a spatially addressable manner. The immobilized molecules are generally referred to as "probes," and the corresponding microspots are called "probe microspots." Immobilization of probe biological molecules is generally two-dimensional in nature, although the immobilization can be achieved by two different mechanisms (physical adsorption versus covalent/affinity attachment).

When the microarray is exposed to a sample of interest, molecules in the sample selectively and specifically binds to their binding partners in the microarrays. The molecules in the sample to be detected and identified are called "targets."

The binding of a "target" to the microspots occurs to an extent determined by the concentration of that "target" molecule and its affinity to a particular probe microspot. In principle, if the target concentrations are known, the binding affinity of the target to different probe microspots can be estimated simultaneously. Conversely, given the known affinities of different targets in a sample for each probe microspot, the amounts of binding observed at each microspot may be directly used to simultaneously estimate the concentrations of multiple targets in the sample. Furthermore, the pattern of binding of a target to different probe microspots can give rise to extremely useful information about the selectivity and specificity of the target to the probes in the microarrays.

To date, biological microarrays can be classified into five general categories based on the species of molecules immobilized on a surface. A first category includes DNA microarrays, which involve a set of nucleic acid molecules tethered to a surface at defined locations. The tethered nucleic acids, such as cDNAs and oligonucleotides, have known sequences and function as "probes." The free nucleic acid sample whose identity/abundance is being assayed is the "target." (See *Nature Genetics* 1999, 21(supplement), pp. 1-60.)

A second category comprises protein microarrays of various kinds. Typically, protein microarrays use immobilized protein molecules of interest on a surface at defined locations. (See review, Wilson, D. S. and Nock, S., "Functional Protein Microarrays," *Curr. Opinion in Chemical Biology* 2001, 6, 81-85.) The immobilized protein molecules have known sequences and function as "probes"; whereas, a "target" is the free biological in a sample whose identity/abundance is being detected. For instance, protein microarrays have been used to identify small-molecule-binding proteins. (Zhu, H., et al., "Global Analysis of Protein Activities Using Proteome Chips," *Science* 2001, 293, 1201-2105.) Arrays of antibody probes also have been used for protein profiling, to measure protein abundances in blood, to measure cytokine abundances, as well as to capture leukocytes/phenotyping leukemias. Arrays of antigen probes have been used for reverse immunoassay to measure auto-immune antibodies and allergies. When the probes are peptides, the peptide microarray may be used to measure protein kinase activities. (Houseman, B. T., et al., "Peptide chips for the quantitative evaluation of protein kinase activity," *Nature Biotechnology* 2002, 20, 270-274.)

Biological membrane microarrays which require that both the receptor molecules of interest and the associated lipid membrane molecules to be immobilized on a surface in confined locations make up a third category. The immobilized receptor molecules are "probes", whereas the "targets" are the free biologicals and chemicals in a sample whose identify/abundance is being detected. Probes can be G protein-coupled receptors (GPCRs) that are embedded in biological membranes to form GPCR arrays, which have been used to study and profile compound specificity and selectivity. (Fang, Y., Frutos, A. G., Lahiri, J., "Membrane Protein Microarrays," *J. Am. Chem. Soc.* 2002, 124, 2394-2395.) Arrays with probes composed of gangliosides that are embedded in lipid membranes have been used to detect toxins in a sample. (Fang, Y., Frutos, A. G., Lahiri, J., "Ganglioside Microarrays for Toxin Detection," *Langmuir,* 2003, 19, 1500-1505.)

Carbohydrate microarrays constitute a fourth category, which involves immobilized oligosaccharides as probes on a surface at defined locations. The "targets" being free in a solution sample are carbohydrate-binding proteins. The carbohydrate microarrays have been used to detect carbohydrate-protein interactions (Fukui, S., Feizi, T., Galustian, C., Lawson, A. M., and Chai, W., "Oligosaccharide Microarrays for High-Throughput Detection and Specificity Assignments of Carbohydrate-Protein Interactions," *Nature Biotechnology,* 2002, 20, 1011-1017.), and to identify cross-reactive molecular markers of microbes and host cells (Wang, D., Liu, S., Trummer, B. J., Deng, C., and Wang, A., "Carbohydrate Microarrays for Recognition of Cross-Reactive Molecular Markers of Microbes and Host Cells," *Nature Biotechnology,* 2002, 20, 275-281.).

A fifth category includes capture reagent microarrays that involve immobilized protein-binding agents of interest on a surface at defined locations. The protein-binding agents are generated from combinatorial methods. The agents may include RNA/DNA aptamers, allosteric ribozymes, and small molecules. (See Wilson, D. S., et al., *Curr. Opinion in Chemical Biology* 2001, 6, 81-85.)

Assay methods to detect the binding of targets to probes in the arrays commonly measure some physical change (such as fluorescence, mass, interfacial properties, luminescence, etc.), which results from the binding of targets to probe microspots directly. These methods generally involve two-units, a probe on the array and a target to be detected in solution. The target molecules are generally labeled by a fluorescent dye. In some other cases, they used a third unit or moiety to amplify the signals. For example, an alternative method to detect targets in a sample after bound to the probe microspots is a "sandwich" assay, which employ a third unit, such as an antibody, that can bind to the target directly. The third unit is fluorescently labeled or conjugated to an enzyme that can produce fluorescence or a luminescent or colored product when supplied with the appropriate substrate.

One problem with which all current biological microarrays face is that they lack a standard by which to evaluate the array quality (i.e., probes in the arrays) as well as normalize the signals generated from the binding of targets. For example, in DNA microarrays scientists have to use a two-color hybridization technique to generate a relative differential expression pattern. Hence, a system that makes use of a universal readout is needed.

SUMMARY OF THE INVENTION

The present invention pertains, in part, to a method to identify and examine the abundance of target molecules in a sample using two-dimensional biological-microarray formats. In principle, the present invention uses a pair of known receptor-ligand interactions, in which a naturally-occurring or synthetic biological or chemical molecule (the "receptor") having a known dissociation constant ($K_d$) to a ligand is employed as a universal readout unit to detect target molecules or compounds in a sample. This universal readout unit does not directly interfere with the binding of targets to their probes in arrays. In other words, the universal readout unit does not bind to the same binding sites or domains of the probes in arrays that are the binding partners of the targets of interest. In contrast, this third unit binds to a common ligand in the arrays, thereby occupying the surface and providing a sterically hindered effect for binding of the targets to the probes in arrays. By doing so, the present invention provides a built-in standard by which to detect or screen, identify, and examine the abundance of various targets in a sample. In principle, a ligand and its complementary universal-readout, binding partner may be adapted to virtually any type of biological microarray format.

The method according to the present invention comprises a number of steps. First, provide a number of biological molecules deposited and immobilized upon a solid or semi-solid substrate. The biological molecules are arranged in at least a microspot, preferably in an array of microspots. Each microspot contains among the biological molecules a co-existant ligand that is common to all of the other microspots. The common ligand functions as a universal adapter for binding of a universal readout protein, in which the protein is included in a sample containing target(s) of interest.

Second, provide a sample containing targets of interest and a universal readout unit that can bind specifically to the common ligand associated with the solid substrate. The universal readout unit may be fluorescently labeled, or conjugated to an enzyme that can produce a fluorescence, luminescent or color product when supplied with the appropriate substrate. The interaction between the universal readout unit and the common ligand should be well characterized. Preferably, the binding constant of the universal readout unit to the common ligand is on the order of a nanomolar or sub-nanomolar range ($1 \times 10^{-5}$–100 nM, preferably ~0.1-~70 nM), such as the strong binding constant of anti-biotin antibody to biotin, protein kinase B to PI(4,5)P2, or cholera toxin to ganglioside GM1.

Third, perform an assay in which the biological targets of interest compete with the labeled universal readout unit in an indirect competitive fashion. That is, the universal readout unit and the targets do not compete for the same binding sites or domains or moieties of probes in arrays, in contrast to direct competition for the same surface area in the probe microspots. Alternatively, one may perform an inhibitory assay, in which an inhibitor directly influences the binding of the targets in a sample to the probe biological molecules in array. One may monitor the binding of the universal readout unit with its corresponding ligand using conventional approaches to detect changes, such as, in fluorescence, or luminescence, or various resonance.

According to the present invention, the universal-readout-unit molecule is much larger physically in size than the common ligand that coexists with probe biologicals in the array. Furthermore, the distribution of the common ligand in each probe microspot should be uniform, and the density of the common ligand should be high enough so that close packing of the universal readout molecule occurs once bound to the microspots. Within the boundaries of a microspot, available surface for binding is limited. A target of interest having similar physical dimensions to that of the universal readout unit will experience spatial or steric hindrance from the universal readout unit, when the target attempts to bind to its corresponding probe biological molecules. Thus, if the larger universal readout molecule binds to the common ligand first, then the target will be blocked from binding to its corresponding biological probe.

In another aspect, the present invention relates to a method for assessing quality control of biological microarray performance. Such a method comprises the steps of: 1) providing a substrate with a number of biological probes immobilized in microspots and having a universal adaptor or common ligand associated with the probes; 2) providing a labeled universal readout unit that can bind with the common ligand; 3) performing an assay by reacting the universal readout units with the biological probes on the substrate, such that the universal readout units bind to the common ligands; and 4) monitoring the relative signal intensity from the label of each universal readout unit. This method may be used to assess the orientation of immobilized biological molecules, as well as examine the spot morphology of the array. One may incorporate on the array an extra microspots, a "control spot," constituted of the common ligands alone. When the labeled universal readout units bind in high-density (e.g., about $\geq 500$ or 1,000 ligands/mm$^2$) to the ligands, the control spot, being an area of closely packed ligands, will exhibit either a higher or the highest signal intensity relative to the other microspots on the array. The relative intensities of microspots will also be important for morphology, as an indication of how well probes and their binding sites are distributed with a microspot. The ligand-only control spot will likely show more uniform signal intensity over its surface area than observed in other microspots.

In yet another aspect, the present invention relates to an assembly with an article and kit for performing high-throughput detection and screening of biological or chemical molecules by means of the present method. The assemblies may comprise particular thematic arrays of biologicals for target identification, including, for example, phosphatidylinositol phosphate (PIP) or sphingolipid microarrays, among others.

Additional features and advantageous of the present invention will be revealed in the following detailed description. Both the foregoing summary and the following detailed description and examples are merely representative of the invention, and are intended to provide an overview for understanding the invention as claimed.

DETAILED DESCRIPTION OF THE INVENTION

Section I

Definitions

Figure 1:
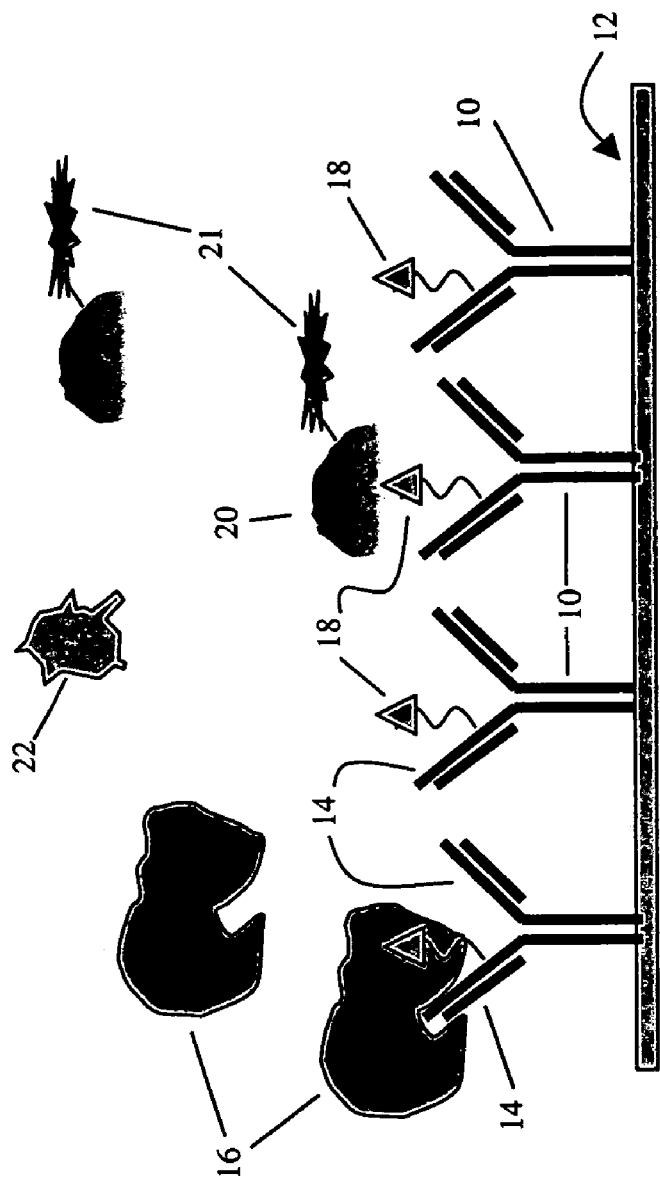
FIG. 1 is a schematic representation of the method according to the present invention. A number of biological molecules or probes (10) are immobilized to a substrate surface (12). Each probe (10) has an associated active or binding site (14) for a corresponding target molecule (16). Each probe (10) also has an associated ligand (18), which binds with a universal readout unit (20), which may be labeled with a fluorescent marker (21). According to a principle of the present invention, a universal readout unit and a target molecule each binds to its corresponding binding partner. Instead of competing for the same binding sites, each molecule competes indirectly with the other for limited space on the surface of a microspot. Once a molecule of one has bound will its binding partner, the surface of the microspot becomes hindered sterically, preventing the binding of the other. In an alternative embodiment, a biological or chemical inhibitor molecule (22) may be present in the sample solution.

Generally, unless defined otherwise, all technical and scientific terms used herein have the usual meaning conventionally understood by persons skilled in the art to which this invention pertains.

As used herein, the term "active site" or "binding site" of a protein refers to the specific area or domain of a protein (e.g., antibody, an enzyme molecule or surface membrane receptor) to which a binding molecule (e.g., substrate or reciprocal ligand) is bound and results in a change in the ligand (e.g., substrate or complex formation with the protein) as a result of ligand binding.

As used herein, the term "biological molecule" refers to any kind of biological entity, including, such as, oligonucleotides, DNA, RNA, peptide nucleic acid (PNA), peptides, proteins, antibodies, membrane protein, lipids, lipid membranes, or cell membranes, or oligosaccharides.

As used herein, the term "biospot," "microspot," or "biosite" refers to a discrete or defined area, locus, or spot on the surface of a substrate, containing a deposit of biological or chemical material.

As used herein, the term "complement" or "complementary" refers to the reciprocal or corresponding moiety of a molecule to another. For instance, receptor-ligand pairs, or complementary nucleic acid sequences, in which nucleotides on opposite strands that would normally base pair with each other according to Watson-Crick-base pair (A/T, G/C, C/G, T/A) correspondence.

As used herein, the term "inhibitor" refers to a biological moiety or chemical compound or molecule that retards the binding kinetics of the probe to the probe's specific paired receptor. The inhibitor binds either reversibly or irreversibly with a particular binding site on the receptor, preventing the normal binding of the probe to the same site. Examples of some types of inhibitors may include: enzyme substrates, small chemical and biological molecules (e.g., pharmaceutical drug compounds, or peptides) that alter biological functions of a protein.

As used herein, the term "probe" refers to either a natural or synthetic molecule, which according to the nomenclature recommended by B. Phimister (*Nature Genetics* 1999, 21 supplement, pp. 1-60.), is immobilized to a substrate surface. The corresponding microspots are referred to as "probe microspots," and these microspots are arranged in a spatially addressable manner to form a microarray. When the microarray is exposed to a sample of interest, molecules in the sample selectively and specifically binds to their binding partners (i.e., probes) in the microarrays. The binding of a "target" to the microspots occurs to an extent determined by the concentration of that "target" molecule and its affinity for a particular probe microspot.

As used herein, the term "receptor" refers to a molecule that has an affinity for a ligand. Receptors may be naturally-occurring or man-made molecules. They may be employed in their unaltered state or as aggregates with other species. Examples of receptors which may be employed according to this invention may include, but are not limited to, antibodies, monoclonal antibodies and antisera reactive with specific antigenic determinants, pharmaceutical or toxin molecules, polynucleotides, DNA, RNA, peptide nucleic acid (PNA), peptides, proteins, cofactors, lectins, polysaccharides, viruses, cells, cellular membranes, cell membrane receptors, and organelles. Receptors are sometimes referred to in the art as anti-ligands. A "ligand-receptor pair" is formed when two molecules have combined through molecular recognition to form a complex.

As used herein, the term "substrate" or "substrate surface" refers to a solid or semi-solid material, which can form a stable support for biospots. The substrate surface can be selected from a variety of materials. For instance, the materials may be biological (e.g., plant cell walls), non-biological, organic (e.g., silanes, polylycine, hydrogels), inorganic (e.g., glass, ceramics, $SiO_2$, gold or platinum, or gold- or platinum-coated), polymeric (e.g., polyethylene, polystyrene, polyvinyl, polyester, etc.), or a combination of any of these, in the form of a slide, plate, film, particles, beads or spheres. Preferably, the substrate surface is two dimensional or flat for the printing of an array of biospots, but may take on alternative surface configurations. For example, the substrate may be textured with raised or depressed regions. Preferably, the substrate surface will have thereon at least one kind of functional or reactive group, which could be amino, carboxyl, hydroxyl, thiol groups, amine-reactive groups, thiol-reactive groups, Ni-chelating groups, anti-His-antibody groups, or the like. More preferably, the surface will be optically transparent and will have surface Si—OH functionalities.

As used herein, the term "target(s)," "target moieties," "biological target," or "chemical target" refers to a solvated particle, molecule or compound of interest in a sample that is to be detected and identified. When a chemical target is involved in an assay, it is preferred that a biological target should be also present in sample for indirect competitive binding.

As used herein, the term "universal readout unit" refers to a receptor that binds with ligands and functions as an indicator of binding. The universal readout unit may be modified, pre-selected or configured to bind with a particular binding domain, ligand or biological located on a probe or substrate surface. The universal readout unit may be a biological or chemical moiety, such as a protein or polymer, or may include, for example, a nanoparticle or bead having a protein or proteins.

As used herein, the term "universal adaptor" or "common ligand" refers to the specific binding partner of a universal readout unit molecule, which as used herein is generally a ligand. The universal adaptor may be customized to a particular biological species of interest.

Section II

Description

The present invention pertains, in part, to a universally applicable method to identify or examine the abundance of target molecules in a sample. The present invention employs a pair of known receptor-ligand interactions, in which either a natural or synthetic biological molecule (the "receptor") has a known dissociation constant ($K_d$) to a ligand. According to an embodiment, the biological molecule (e.g., a labeled protein or polymer molecule) functions as a universal readout unit or indicator for detecting unknown target molecules or compounds in a sample. The ligand co-exists among surface immobilized biological probes and is common to all of the probe microspots when used in a two-dimensional (2-D) array format. The distribution of the common ligand in each probe microspot should be uniform, and the density of the common ligand should be sufficient so that close packing of the universal readout units occurs once they become bound to the microspots.

Unlike conventional competitive binding assays, this universal readout unit does not directly interfere with the binding of target moieties to their corresponding probes. Indirect or parallel competition between the target and the readout unit is used. That is, the universal readout unit does not bind to the same binding sites or domains (i.e., active site(s)) of the probes as the targets do. Rather, the universal readout unit binds to the common ligand dispersed among the probes. According to the present invention, the universal readout unit is much larger physically in size than the ligand. Each universal readout molecule or receptor has a size in the range of about 2 nm to about 100 nm. Preferably, the universal readout unit is about 3-30 nm, or more preferably about 4-20 nm in size. Actual size of a receptor, however, will be relative and dependent on the size of the ligand and/or target molecule. For best results, the target of interest and universal readout unit preferably are similar in size. Within the confinement of a microspot, available surface is limited. Thus, if the larger universal readout unit binds to the common ligand first, occupying the surface and creating spatial or steric hindrance, then a target moiety of interest attempting to bind to its corresponding probe will be retarded from binding to the probe. According to this mechanism, the present invention provides a built-in standard to identify or detect the abundance of targets in a sample.

In part, the present invention expands upon research that was described in U.S. Patent Application Publication Nos. 2002/0019015, and 2002/0094544, and U.S. Provisional Patent Application 60/392,275, the content of each is incorporated herein by reference, and extends the usefulness of biological-membrane microarray formats to several new applications. Among the several advantages of the present method, the ability to use a single kind of molecule as a "universal readout" for the identification of all kinds of targets in general, such as listed below, is one of the more important. Since one needs only to detect the signal from the labeled universal readout molecules, one need not label the targets, even though all the targets can be labeled differently to allow investigators to cross-examine individual assay results. The present method can be used for virtually all kinds of two-dimensional (2-D) microarray or particle- or bead-based assay formats. Hence, the method can provide a standard to directly profile targets to different probes in the arrays.

A probe biological may be selected from a variety of biological or chemical molecules including, but not limited to, an oligonucleotide, a soluble protein, an antibody, an oligosaccharide, a peptide, or a biological membrane that contains a receptor of interest. A common ligand, such as a biotin-moiety, may be attached to the biological probes on the array. In particular embodiments, when the probe biological in array is a biological membrane, the common ligand may be a biotinylated lipid molecule, a ganglioside molecule, or a phosphoinositide. Alternatively, when the probe biological in array is a protein or an antibody, the common ligand may be, for instance, a His-tag, a FLAG-tag, or a protein domain.

Hence, in terms of a two-dimensional microarray format, the present invention relates to oligonucleotide microarrays, protein microarrays, oligosaccharide microarrays, and biological membrane microarrays. The microarrays are fabricated on the surface of a solid substrate, preferably coated with a material that enhances the immobilization and attachment of the probe biological moieties. The biological moieties may be attached to the surface by means of one of two fundamentally different mechanisms. These being: (1) physical adsorption through electrostatic interaction, hydrophobic interaction, hydration force or any combinations of the above; or (2) covalent attachment or affinity immobilization based on receptor-ligand interactions, such as the immobilization of biotinylated proteins onto streptavidin-coated surface and immobilization of His-tagged proteins onto nickel ion-chelating surfaces. A preferred attachment method for immobilization of probe biological moieties upon a surface depends on the particular biological probe species. For instance, with respect to oligonucleotide microarrays and oligosaccharide microarrays, the probe molecules preferably are coupled covalently to a surface. For protein microarrays, however, the probe molecules preferably are bound to a surface based on affinity immobilization because affinity immobilization can possibly create preferred orientations of the probe proteins once immobilized.

Ligands

In theory, any kind of ligand binding assay that uses an immobilized capturing molecule for the detection of the binding of analyte from a solution can be miniaturized. Within the last few years, methods based on microarray technology have been extended from the analysis of gene expression level and single nucleotide polymorphisms (SNPs) using DNA microarrays to the analysis of proteins using protein microarrays, and novel applications emerged. Protein microarrays offer the fascinating possibility to study protein interactions in a massively parallel fashion, including protein-protein, enzyme-substrate, protein-DNA or protein-drug interactions.

According to the present invention, various kinds of ligand species may be used with various kinds of probe moieties. A pre-selected species of ligand, coexisting with probes and is common to all of probe microspots in an array, is referred to as a "common ligand." This common ligand is used to facilitate the binding of a universal readout unit to the surface of each probe microspot in an array. For instance, when the probe is a oligonucleotide, a oligosaccharide, a protein, an antibody, or a peptide, the common ligand may be a biotin-moiety attached to the probe. In another embodiment, when the probe is a biological membrane containing a glycolipid, such as a ganglioside or a phosphoinositide (PIP), or a membrane-bound protein such as a G protein-coupled receptor or a ion channel, the common ligand may be a biotinylated lipid molecule, a ganglioside molecule, or a phosphoinositide. Further, in another embodiment, when the probe biological in array is a protein, a recombinant protein, or a fusion protein, the common ligand may be a His-tag, a FLAG-tag, or a protein domain.

As illustrated, even though the underlying biological molecule on an array may change, the common ligand is used as a universal adapter, which can recognize and bind to a universal readout unit. In other words, even as the probe moieties may vary from one type of array to another, the ability of the universal readout unit or protein to bind is not adversely effected, since the readout unit binds not with the probe molecules themselves, but rather with their associated ligand. Hence, a ligand and its complementary universal-readout, binding partner is adaptable to virtually any type of biological microarray.

Universal Readout Units

As mentioned before, the universal readout unit or protein does not directly interfere with the binding of targets to their probes in array, since it does not bind to the same binding sites or domains of the probes in array as targets of interest do, but rather to the common ligands. The universal readout unit complements the ligand. According to an embodiment, when the common ligands is a biotin-moiety of a probe biologicals in array, or a biotinylated lipid molecule co-existed in probe biological membranes in array, the universal readout unit may be an anti-biotin antibody or a streptavidin. In another embodiment, when the common ligand in a biological membrane is a ganglioside molecule, the universal readout unit may be a toxin (e.g., cholera toxin, while the ganglioside is GM1). In another example, when the common ligand in biological membrane is a phosphatidylinositide phosphates (PIPs), the universal readout protein may be a PIP-binding protein (e.g., protein kinase B, while the PIP is PI (4,5) P2). When the common ligand in a protein array is a His-tag, or a FLAG-tag, the universal readout protein may be, respectively, an anti-His antibody, or an anti-FLAG antibody.

Because of the two-dimensional nature of virtually all biological microarrays, one could use a labeled universal readout unit that can bind to all of the probe microspots. Preferably, the universal readout protein is fluorescently labeled, or conjugated to an enzyme that can produce a fluorescence, luminescence or color product when supplied with an appropriate substrate. The interaction between the universal readout protein and the common ligand should be well characterized. Preferably, the kinetic binding constant of the readout protein to the common ligand is like that for the binding of anti-biotin antibody to biotin, protein kinase B to PI(4,5)P2, or cholera toxin to ganglioside GM1. In particular, in the range of about $1 \times 10^{-5}$ nM to about 50 nM, more preferably in the range of about 0.03 nM to about 15 nM, most preferably about 0.05 nM to about 10 nM.

Substrates

The substrates used for the present invention subject arrays comprise at least one surface on which the pattern of probe spots is present. The surface may be smooth or substantially planar, as with a glass slide, or have irregularities, depressions or elevations, such as in a porous substrate. In an embodiment, preferably, the surface of a substrate is substantially flat, or ultra-flat, with an average surface roughness of less than about 10 nm. The average surface roughness is preferably less than about 5 nm, more preferably less than about 3 nm, and most preferably ranges from about 0.1 nm to about 2 nm per $1 \times 1$ μm$^2$. Of course, actual optimal surface roughness is related to the size of the target of interest to be analyzed. Further, the surface on which the pattern of spots is present may be modified with one or more different layers of compounds or functional groups (e.g., hydroxyl or carboxyl groups, anhydride, amine or silane groups (e.g., poly-lycine or γ-aminopropylsilane (GAPS)-coated) on glass, or thiol-groups on gold) that serve to modify the properties of the surface in a desirable manner.

The substrate may comprise a ceramic substance, a glass, a metal, a metallic oxide, a crystalline material, a plastic, a polymer or co-polymer, any combinations thereof, or a coating of one material on another. Such substrates include for example, but are not limited to, (semi) noble metals such as gold or silver; glass materials such as soda-lime glass, aluminosilicate, boroaluminosilicate or borosilicate glass, Vycor® glass, quartz glass; metallic or non-metallic oxides; silicon, monoammonium phosphate, and other such crystalline materials; transition metals; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, polystyrenes, polypropylene, polyethyleneimine; copolymers such as poly(vinyl acetate-co-maleic anhydride), poly (styrene-co-maleic anhydride), poly(ethylene-co-acrylic acid) or derivatives of these or the like.

The substrate may take a variety of configurations ranging from simple to complex, depending on the intended use of the array. For instance, the substrate could have an overall rectangular or circular configuration, such as a slide, disc, or plate. According to an embodiment, the substrate may be a well-bottom in a microplate having various numbers of wells (e.g., 96, 384, 576, 1536, etc.). Other configurations may include particle or beads.

An array of the present invention optionally may further comprise a coating material on the whole or a portion of the substrate comprising the probe microspots. Preferably the coating material enhances the attachment of probe biological moieties. Most preferably the coating material permits the oriented attachment of probes.

Section III

Microarrays

Biological microarrays of the present invention may include, but are not limited to, oligonucleotide microarrays, protein microarrays, biological membrane microarrays, and oligosaccharide microarrays. The biological microarrays are fabricated on a surface of solid substrate, as described above, in which the microarrays are two-dimensional in nature. The surface is preferably coated with a material that enhances the immobilization and attachment of the biological probes.

Biological molecules can be attached to the surface through two different mechanisms. To reiterate, these mechanisms are: (1) physical adsorption through electrostatic interaction, hydrophobic interaction, hydration force, or any combination thereof; or, (2) covalent attachment or affinity immobilization based on receptor-ligand interactions. An example of the second mechanism includes the immobilization of biotinylated proteins onto streptavidin-coated surface and immobilization of His-tagged proteins onto nickel ion-chelating surfaces. The actual preferred attachment method for immobilization of probe biological moieties onto a surface depends on the particular species of probe. For instance, with respect to oligonucleotide microarrays and oligosaccharide microarrays, the probe molecules are preferably covalent-coupled to a surface. For protein microarrays, however, the probe molecules are preferably bound to a surface based on affinity immobilization, because affinity immobilization could give rise to a preferred orientation of the probe proteins once bound.

Section IV

Examples of Microarray Formats & Applications

Having described the general concept of the present invention, the universal detection method may be applied to numerous uses for assaying a variety of biological molecules. The following examples of ligand-associated thematic arrays are only some of the many possibilities for identifying biological or chemical targets to which the present invention may be applied.

A. Target Identification Using Protein Capture Reagent Microarrays

Protein microarray technology has been emerging as a promising and powerful tool to study many components simultaneously, thereby allowing one to learn how proteins interact with each other, as well as with non-proteinaceous molecules, to control complex processes in cells, tissues and even whole organisms. Protein microarrays has been applied to measure the abundance, modification, activity, localization and interaction of all the proteins in a sample (e.g., protein profiling—an application referred to as quantitative proteomics), and to identify putative substrates for enzymes or putative interactions between proteins (e.g. compound screening for drug discovery—an application referred to as functional proteomics). Quantitative proteomics involves the use of protein-detecting microarrays that comprises many different affinity reagents such as antibodies and antigens arrayed at high spatial density on a solid substrate. Each agent captures its target protein from a complex mixture (such as serum or cell lysate), and the captured proteins are subsequently detected and quantified. In functional proteomics, the proteins themselves, rather than affinity reagents, are arrayed on a solid support. An advantage of studying proteins in an array format is that the investigator can control the conditions of the experiment. This includes not only factors such as pH, temperature, ionic strength and the presence or absence of cofactors, but also the modification states of the proteins under investigation. A unique advantage of protein function microarrays is that they can be used to study the interaction of proteins with non-proteinaceous molecules, including nucleic acids, lipids and small organic compounds.

On any protein capture reagent microarray, for instance, one may identify a target without the need to directly label the targets if the physical size of the target is bigger than the probe on the microarray. As illustrated schematically in FIG. 1, an adapter ligand 18 is part of the probe biological molecule 10 immobilized on the surface 12 in each microspot. The binding partner for adapter ligand 10 is a labeled protein molecule 20 with a fluorophore or some other tag 21, which serves as the universal receptor that can act as a universal readout 20$a$ or marker. The labeled receptor specifically binds to its particular kind of adapter ligand on all the probes. Each biological target, chemical, or organism of interests can specifically bind to the probe biologicals in the microspots. The probe biological molecule in the array is preferably an antibody, a recombinant protein, a peptide, an oligosaccharide, or a nucleic acid or peptide aptamer. An inhibitor molecule 22 could also be included for performing an inhibitory assay.

In one embodiment, the adapter ligand is preferably biotin moieties in the biotinylated probe biologicals, whereas the universal readout is anti-biotin-antibody or streptavidin. In another embodiment, the adapter ligand is preferably a His-tag or a FLAG-tag or a fusion domain of a recombinant protein, whereas the universal readout is an anti-His, an anti-FLAG, or a protein or antibody that binds to the fusion domain specifically, respectively.

An advantageous use of the present inventive universal readout assay is to test for microarray quality. One can compare the binding of universal readout units to microspots comprising both probe biological molecules and adapter ligands with the binding of universal readout units to a control spot containing only the ligands. That is, one can measure the orientation of biological molecules (generally proteins and antibodies) as well as examine the spot morphology, given that the location of the adapter ligand or domains in the probe proteins is known. For example, when a protein or antibody is deposited and immobilized, its domain or active binding site may be oriented either toward or away from the substrate. If the active site has an orientation away from the substrate, then the active site will be more accessible to either target molecules or universal readout units. If, on the other hand, the active site has an orientation turned toward the substrate, the active site is more blocked from binding with either target molecules or universal readout units. Hence, when labeled units attach, a microspot in which a greater percentage of immobilized biological probes in an open, accessible orientation should exhibit higher signal intensity than one having more biological probes in an inaccessible orientation. A percentage of binding is measurable. Further, since the domain of each protein or antibody is different, the present inventive concept simplifies the comparison process by using the same ligand or universal adaptor (e.g., a His-tag, a Flag-tag) and its complementary universal readout unit.

B. Target Identification Using Glycolipid Microarrays

The cell surfaces of many organisms contain glycolipid and glycoprotein molecules, which serve as recognition sites. Glycolipid and glycoprotein molecules, respectively, have either a phospholipid or a protein structure, which is embedded within the cell membrane, and at least one carbohydrate chain extending from the cell surface. The carbohydrate groups provide part of the structure that enables the glycolipid and glycoprotein molecules to perform recognition; reception and adhesion functions.

Living cells can recognize numerous signals that originate from other cells and their environment through molecules associated on the cell surfaces, and respond to the external signals appropriately so as to direct and regulate normal cell growth, development, and organization. For example, toxins are one of the important groups of the various biological or chemical agents that may affect cells. Toxins can target a variety of molecules on the surface of a host cell. For instance, some toxins, such as diphtheria toxin (*Corynebacterium diphtheriae*) and anthrax.toxin (*Bacillus anthracis*), bind to proteins on the cell surface during pathogenesis. Other bacterial toxins (e.g., from the genera *Streptococcus, Bacillus, Clostridium,* and *Listeria*) target cholesterol molecules. A large number of bacterial toxins target carbohydrate-derivatized lipids on the cell surface, often with high specificity. These lipids, glycosylated derivatives of ceramides, referred to as sphingoglycolipids, can be classified into cerebrocides (ceramide monosaccharide), sulfatides (ceramide monosaccharide sulfates), and gangliosides (ceramide aoligosaccharides).

Figure 2:
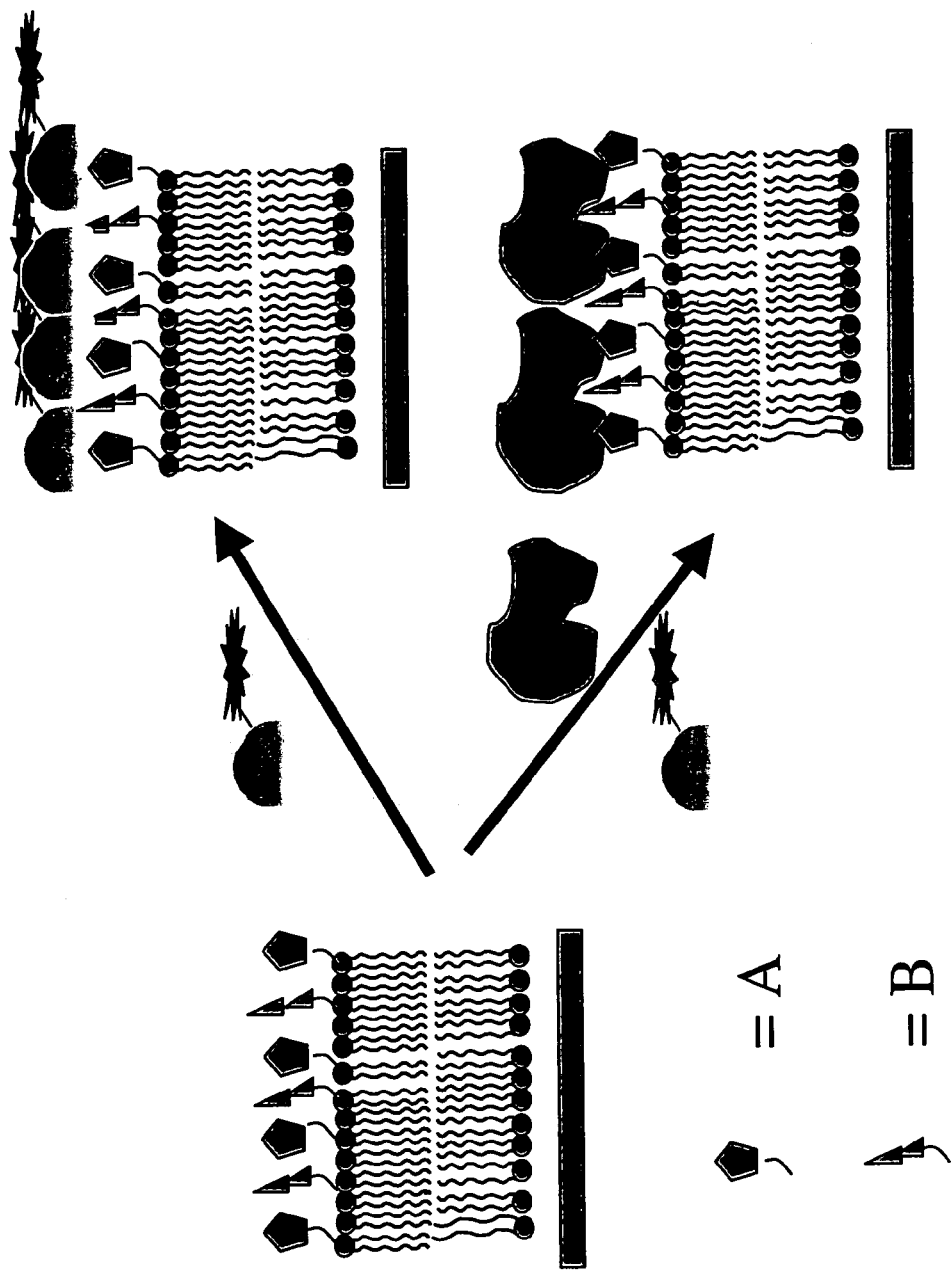
FIG. 2 shows an embodiment of the present invention for identifying membrane receptor-binding proteins or bio-organisms. In a microspot, a common ligand (A) is included among biological probes containing a lipid-associated binding site or receptor of interest (B). The binding partner for common ligand A is labeled and used as a universal readout unit. The biological or chemical target of interest competes with the universal readout unit (e.g., protein).

Further, cell-surface molecules experience extensive interaction with intracellular proteins. For example, agonist-binding G protein-coupled receptors (GPCRs) interact and activate heterotrimeric G proteins, which then regulate the activity of specific cellular effectors. Beyond the G protein paradigm, GPCRs can interact with members of diverse families of intracellular proteins. Among these proteins may include, for instance, polyproline-binding proteins such as those containing Sh3 domains, arresting, G protein-coupled receptor kinases (GRK), small GTP-binding proteins, SH2 domain-containing proteins, or PDZ domain-containing proteins. Membrane domains containing phosphatidyllinositol phosphate (PIP) are targets for many pleckstrin homology (PH)-containing proteins such as PLCδ and ARF protein exchange factor GRP1. A general concept is depicted schematically in FIG. 2, relating the use of universal readout for target identification using biological membranes.

Example 1

Toxin Detection Using Ganglioside Microarrays

Many prokaryotic and eukaryotic animals and plants produce toxins, which can have harmful and sometimes lethal effects on other living organisms. All animal toxins target a cell surface protein that is involved in an essential cell function. Nearly all toxins targets cell-surface proteins are ligands of ion channels, which regulate rapid transport activity into or out of the cell. When toxin molecules bind to the cell surface proteins, the ion channels, which the proteins control, are inactivated, and consequently the toxin interferes with the biochemical mechanisms for important specific cellular functions, such as neurological or muscular functions. Various kinds of toxins can target a specific function For example, just to name a few, tetrodotoxin, saxitoxin, bactrachotoxin, grayanotoxin, veratridine, actonitine, scorpion and sea anemone venom can attack different sites of sodium channels and block their function; and, some other toxins including apamin and related peptides, scorpion charybdotxins, dendrotoxins, hanatoxins, sea anemone toxins target specifically potassium channels. Other toxins such as hololena or calcicludine target calcium channels, while toxins such as bungarotoxin and conantokins target, respectively, nicotinic acetylcholine receptors and glutamate receptors.

Figure 3:
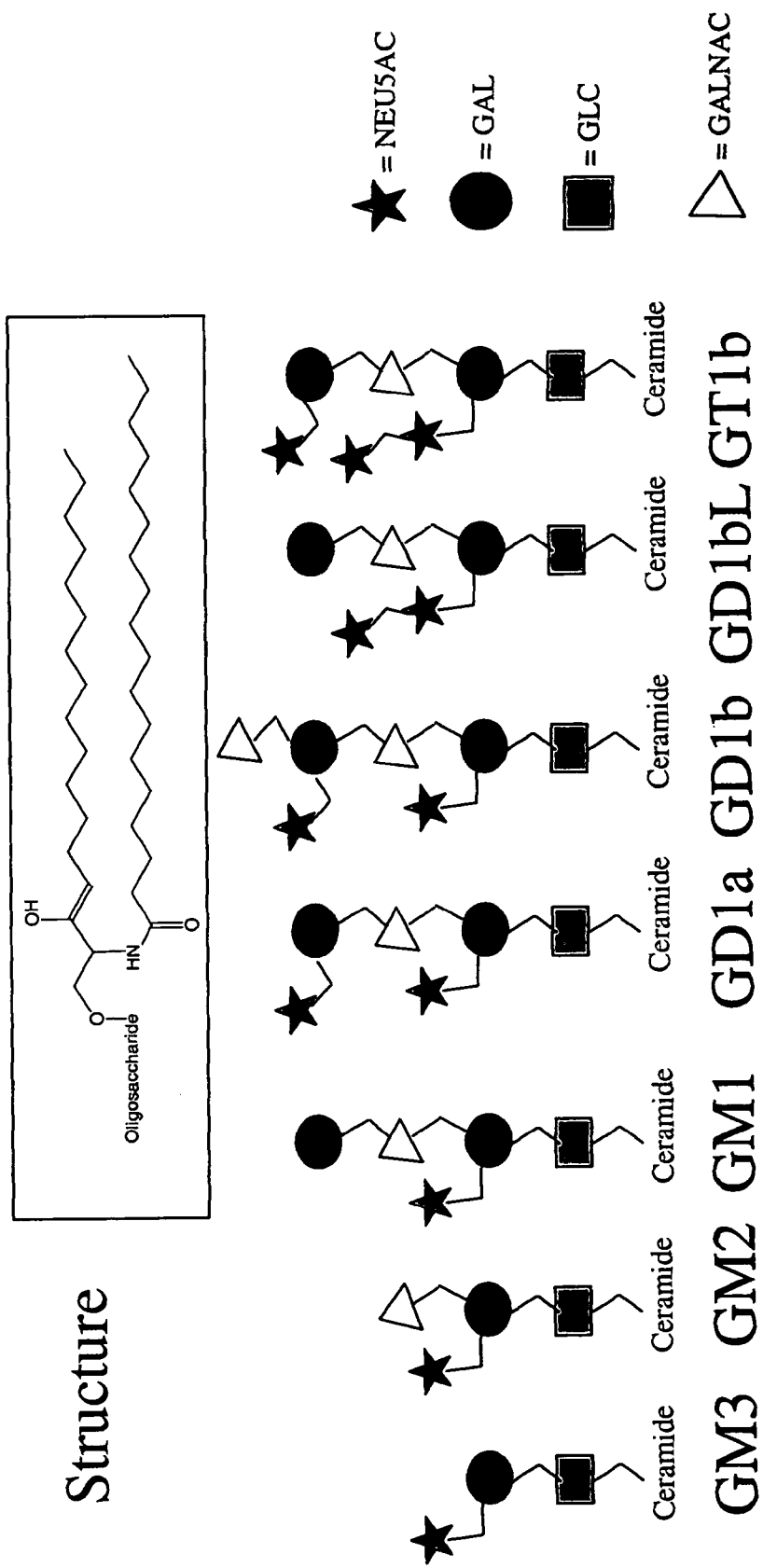
FIG. 3 shows structure of typical gangliosides related to this invention.

Alternatively, some other cell surface molecules may be targets of toxin binding. For example, cholesterol is the target molecule for bacteria from the genera *streptococcus, bacillus, clostridium,* and *listeria*. A large number of bacterial toxins target carbohydrate derivatized lipids on the cell surface, often with high specificity. These lipids, glycosylated derivatives of ceramides referred to as sphingoglycolipids, can be classified into cerebrocides (ceramide monosaccharide), sulfatides (ceramide monosaccharide sulfates) and gangliosides (ceramide oligosaccharides). One of the best-studied examples of toxin-ganglioside interactions is the binding of the (cholera) toxin produced by *Vibrio cholerae* to the ganglioside GM1. The specificity of toxin-carbohydrate interactions is well demonstrated by differences in the binding epitopes between the tetanus and cholera toxins. The tetanus toxin (produced by *Clostridium tetani*) binds specifically to the ganglioside GT1b. Some typical gangliosides are shown in FIG. 3.

In one aspect, one may describe the use of microarrays of lipids containing gangliosides for toxin detection and ganglioside-binding proteins, as well as screening of compounds as potential toxin inhibitors. In one embodiment, a microarray having different lipid compositions is fabricated. The lipid compositions may include a synthetic lipid such as DLPC (dilaurylphosphatidylcholine), a mixture of different synthetic lipids such as dipalmitoylphosphatidylcholine (DPPC)/dimyristylphosphtidylcholine (DMPC), and a synthetic host lipid doped with toxin-binding receptors. The host lipid can be any given lipid such as a synthetic lipid or a natural lipid (e.g., egg PC). The toxin-binding receptor includes a ganglioside such as GM1 and GT1b, or a ceramide, or a cholesterol, or a cerebroside. This type of microarray is preferably used to identify bacterial toxin and screen compounds that interfere with the binding of toxins to these biological membranes.

In another embodiment, the particular common ligand on ganglioside microarrays is preferably a lipid molecule presenting a binding moiety for the universal readout unit. The lipid molecule is preferably a biotinylated lipid molecule, a ganglioside molecule such as GM1, or a phosphoinositide such as PI(4,5)P2. Correspondingly, the universal readout unit is preferably an anti-biotin-antibody, a well-known toxin (e.g., cholera toxin), or a PIP binding protein (e.g., protein kinase B).

Example 2

Identification of PIP-Binding Proteins Using Phosphoinositol Microarrays

Figure 4:
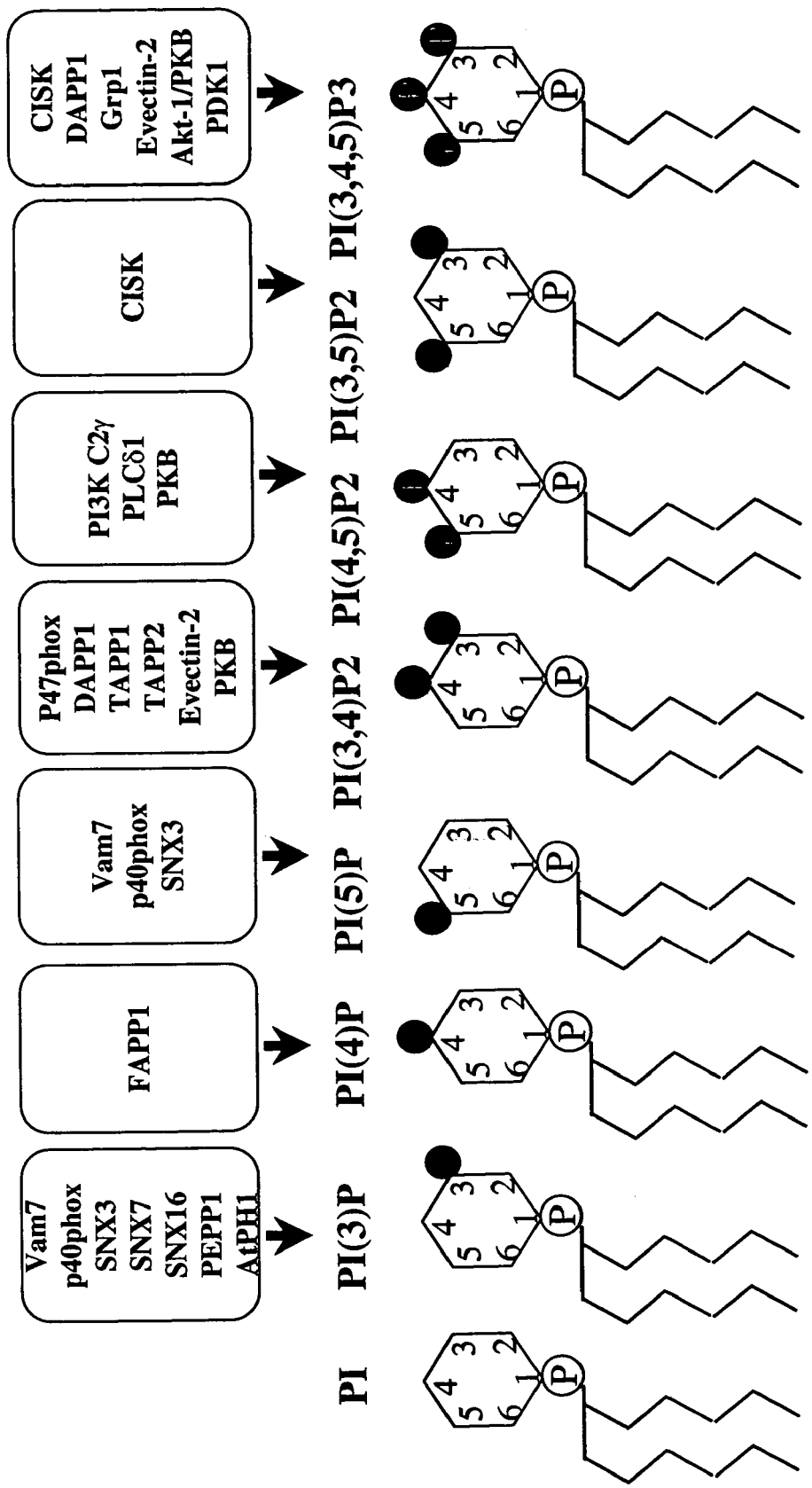
FIG. 4 shows structures of typical phosphatidylinositol phosphates and examples of proteins that specifically bind to different PIs.

Phosphoinositol lipids and their phosphorylated derivatives, the phosphoinositides (PIs), have been recognized as versatile secondary messengers and modulators of lipid membrane composition in all eukaryotes. The PIs play important roles in regulation of cellular processes via receptor-mediated membrane signals. These signals affect the intracellular localization and/or biological properties of effector proteins involved in intracellular vesicle trafficking, cytoskeletal regulation, cell growth, apoptosis, exocytosis, endocytosis, neuronal signaling, regulation of calcium, cAMP and leptin uptake. Phosphatidylinositol (PtdIns) contain five hydroxyl groups, all of which can be reversibly phosphorylated in mammalian systems, such as depicted schematically in FIG. 4. The biological versatility of PtdIns is derived from their ability to participate in reversible phosphorylation. The most abundant PtdIns in mammalian cell membranes is 1,2-diacyl-glycero-3-phospho-D-1-myo inositol, which represents 5-20% of total cell glycerophospholipids.

Phosphoinositide kinases (PIKs) synthesize Phosphatidylinositol phosphates (PIPs) by adding phosphate groups to pre-existing inositol glycerophospholipids. Protein targeting is currently a major research area in inositol signaling. The importance of membrane targeting by PIs is exemplified by the number of human genetic diseases linked to defects in PI signaling including cancer, immunodeficiency disorders (such as X-linked agammaglobulinemia and chronic granulomatous disease), myotubular myopathy, kidney and neurological diseases (oculocerebro-renal syndrome of Lowe). The biological activity of PIs can be spatially controlled by regulating the enzymes that synthesize (kinases) and degrade (phosphatases and lipase) the phosphorylated inositols. In the past decade, researchers have identified protein domains that specifically bind PIs and have determined the localization of proteins to the site of action. These PI-binding motifs include the PH (Pleckstrin homology), FYVE (Fab1p/YOTP/Vac1p/EEA1), ENTH (Epsin NH2-terminal homology), PX (Phox homology) and tubby domains. These domain-containing proteins account for several hundred proteins in mammalian cells. In addition, many of these proteins can interact with other proteins to form functional complexes and/or relay signaling cascades. Thus, thousands of proteins could be regulated directly or indirectly by the various PIs. Therefore, a systematic approach to examine PI-binding proteins is needed.

Figure 5:
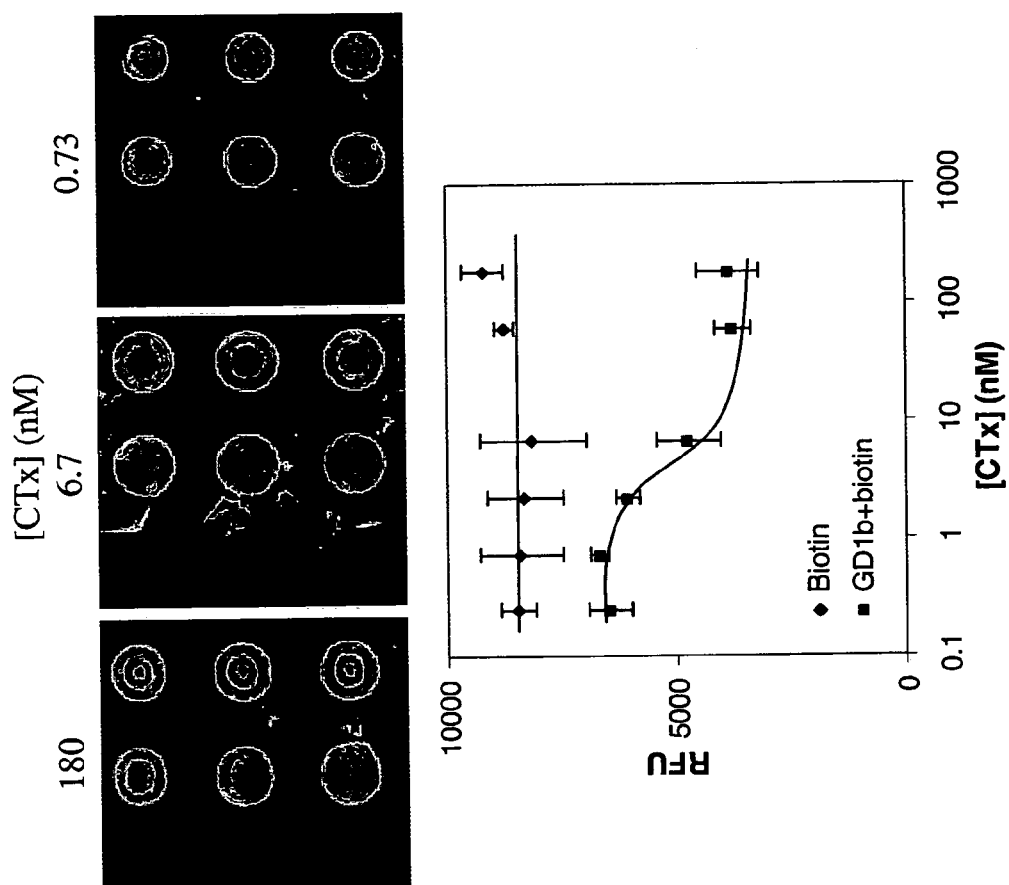
FIG. 5 shows in a series of panels, A-D, the dose response of unlabeled cholera toxin B on the binding sites of cy3-labeled streptavidin on a gama-amino-propylsilane-(GAPS)-coated laboratory slide. Panels A-C are the fluorescence images of the microarrays. Panel D is a graphical plot of the relative fluorescence intensity of DLPC/biotin-DHPE microspots (diamonds), and DLPC/GD1b/biotin-DHPE microspots (squares) as a function of the concentration of unlabeled cholera toxin.

The present inventive concept may be applied to the use of microarrays of lipids containing PIs for systematic screening of PI-binding proteins and their co-factors. According to an embodiment, a thematic array composed of phosphatidylinositol phosphate (PIP) in the absence and presence of host lipids may preferably be used to identify PIP-binding proteins. The PIPs may include PtdIns, PtdIns(3)P, PtdIns(4)P, PtdIns(5)P, PtdIns(3,4)P2, PtdIns(3,5)P2, PtdIns(4,5)P2, PtdIns(3,4,5)P3 (FIG. 5). The host lipid is a synthetic lipid such as DLPC (dilaurylphosphatidylcholine), a nature lipid such as egg PC, or a mixture of different lipids such as dipalmitoylphosphatidylcholine (DPPC) and dimyristylphosphtidylcholine (DMPC).

In an embodiment, the particular common ligand on phosphoinositol microarrays is preferably a lipid molecule presenting a binding moiety for the universal readout unit. The lipid molecule is preferably a biotinylated lipid molecule, a ganglioside molecule such as GM1, or a phosphoinositide such as PI(4,5)P2. Correspondingly, the universal readout unit is preferably an anti-biotin-antibody, a well-known toxin (e.g., cholera toxin), or a PIP binding protein (e.g., protein kinase B).

Example 3

Identification of Lipid-Raft-Binding Proteins Using Sphingolipid Microarrays The bioactive sphingolipid metabolite sphingosine 1-phosphate (S1P) functions as both a first messenger and a second messenger that play very complicate roles in signaling cascades of apoptosis, proliferation, and stress responses. S1P is the natural agonist for members of the S1PR family of G protein-coupled receptors (GPCRs), thereby regulating cell movement by binding and activating these receptors. Furthermore, S1P can also function as a second messenger important for regulation of calcium homeostasis and suppression of apoptosis.

Sphingolipids were generally believed to protect the cell surface against harmful factors in the environment by forming a mechanically stable and chemically resistant outer leaflet of the plasma membrane lipid bilayer. Evidence shown that sphingolipids are synthesized in the ER1 and the Golgi compartments but are enriched in plasma membrane and endosomes where they perform many of their functions. Thus, sphingolipids travel between organelles via transport vesicles and via monomeric transport through the cytosol. Furthermore, some sphingolipids efficiently translocate across cellular membranes.

A growing body of evidence suggests that sphingolipids (glycosphingolipids and sphingomyelins) can combine with cholesterol to form clusters in biological membranes. The clusters (domains) are less fluid (liquid-ordered) than the bulk liquid-disordered phospholipids based on diacylglycerol. The diameter of sphingolipid/cholesterol rafts on the outer surface of the plasma membrane was estimated to be small (i.e., on the order of tens to hundreds of nanometers (nm)) compared with that of cells (on the order of tens of microns (μm)) and to occupy some 10% of the cell surface. These sphingolipid-based microdomains or "rafts" play a key role in processes such as membrane trafficking, signal transduction, and protein sorting. To fully grasp raft function, it will be necessary to identify and characterize the different types of raft, to understand the mechanism of rafts interacting with a protein of multiple transmembrane domains and protein-protein complexes.

Recently, researchers have applied model lipid membranes to establish the principles by which mixtures of sphingolipids, unsaturated glycerophospholipids, and cholesterol can segregate into two fluid phases. In this case, the sphingolipids and part of the cholesterol segregate into a "liquid-ordered" domain from the unsaturated lipids in a "liquid-disordered" phase (Spiegel, S., and Milstien, S. (2000) *Biochim. Biophys. Acta* 1484, 107-116). By using model lipid membranes to constitute lipid rafts with various compositions, one would be able to gain understanding the molecular mechanism how a protein locates to domains, and to identify new intracellular or extracellular targets that bind to these domains.

In an example, a researcher may wish to employ a lipid-raft microarray in combination with universal readout to identify sphingolipid-binding proteins. According to an embodiment, a theme array made-up of sphingolipids in the presence of host lipids can be fabricated. The sphingolipids may include sphingosine, sphingosine phosphate, phytosphingosine, sphingomyelin, sphingosylphosphocholine, sulfatide, ceramide, as well as their glycosylated derivatives (i.e., sphingoglycolipids). The host lipids may include a synthetic lipid such as dilaurylphosphatidylcholine (DLPC), a nature lipid such as egg phosphatidylcholine (egg PC), or a mixture of different lipids such as dipalmitoylphosphatidylcholine (DPPC)/ dimyristylphosphtidylcholine (DMPC). This type of microarray is preferred. As an alternative embodiment, a theme array having sphingolipids in the absence of host lipids may be employed to identify sphingolipid-binding proteins.

Preferably, the common ligand associated on aphingolipid microarrays may be a lipid molecule presenting a binding moiety for the universal readout unit. The lipid molecule is preferably a biotinylated lipid molecule, a ganglioside molecule, or a phosphoinositide such as PI(4,5)P2. Correspondingly, the universal readout unit is preferably an anti-biotin-antibody, a toxin (e.g., cholera toxin), or a PIP binding protein (e.g., protein kinase B).

C. Ligand Screening Using Ligand-Gated Ion Channel Microarrays

Using a theme array containing a variety of ion channels integrated in biological lipid membranes, one may identify animal toxins and screen compounds that interfere with the binding of toxins to these ion channels. The ion channels may include sodium channel, potassium channel, calcium channel, acetylcholine receptor, ryanodine receptor calcium channel, glutamate receptor, and any given combination of these ion channels. These ion channels can be either in the form of membrane preparation that is separated from certain cell lines, or in the form of re-folded protein in liposomes. The re-folded ion channels can be made using state-of-the-art methods.

According to an embodiment, the common ligand on the ion channel microarray is preferably a biotin moiety located inside the channel. The ligand is associated with the channel in a way that a universal readout protein can compete with the ligand binding to the same channel. Correspondingly, the universal readout protein is preferably an anti-biotin antibody.

In another aspect, the present invention relates to an assembly with an article and kit including ligands and complementary universal readout units for performing high-throughput detection and screening of biological or chemical molecules by means of the present method. The assemblies may comprise microarrays as described herein or particular thematic arrays of biologicals for target identification, including, for example, phosphatidylinositol phosphate (PIP) or sphingolipid microarrays, among others. According to other embodiments, a microarray having any of the foregoing ligand-associated substitutents or a combination of the biological membranes may be used to screen any given set of toxins.

Section VII

Empirical Examples

Toxin Detection Using Ganglioside Microarrays (1) Materials and Methods

Dilaurylphosphatidylcholine (DLPC), and gangliosides (GD1b) were purchased from Sigma Chem. (St. Louis, Mo.). Biotin-X-DHPE was obtained from Molecular Probes (Eugene, Oreg.). Cholera toxin subunit B and Cy3-labeled streptavidin was also purchased from Sigma. Gamma-aminopropylsilane-coated (GAPS) slides were used.

Following a standard sonication method, we produced small vesicles of DLPC lipid doped with and without 4% ganglioside (mole ratio) in the presence and absence of 4% biotin-x-DHPE. The sonicated vesicles were employed for the fabrication of lipid microarrays using a quill-pin printer (Cartesian Technologies Model PS 5000) equipped with software for programmable aspiration and dispensing. Before printing, mixtures of DLPC (1 mg/mL) with 4 mol % ganglioside (GT1b) and/or 4 mol % biotin-X-DHPE in 20 mM phosphate buffer (pH 7.4) was sonicated to clarity. For printing, 25 µL of each lipid solution was added to different wells of a 384 well microplate. Replicate microspots were made using a single insertion of the pin into the solution. To prevent contamination from carryover between different lipid solutions, an automatic wash cycle was incorporated, which comprised consecutive washes of the pin in ethanol and water. After printing, the arrays were incubated in a humid chamber at room temperature for about one (1) hour and then used for toxin binding experiments.

For the binding assays, each individual array was incubated with 20 µL of a solution containing unlabeled toxin (0-180 nM) in the presence of 1 nM Cy3-labeled streptavidin. The binding buffer used for all experiments was 20 mM phosphate buffer (pH ~7.4, 0.2% BSA). Arrays were imaged using a GenePix 4000B fluorescence scanner.

(2) Results and Discussion

A microarray of three different lipid compositions—1) DLPC, 2) DLPC/4%biotin-DHPE, and 3) DLPC/4%biotin-DHPE/4% GD1b—was fabricated as in the order shown in FIG. 5, from left to right column within a grid. The effect of unlabeled cholera toxin sub-unit B on the binding of Cy3-avidin was examined. Results show that the cholera toxin significantly affects the binding of cy3-avdin to the microspot containing GD1b and biotin-x-DHPE, but not to the spots containing Biotin-X-DHPE only. The IC50 value was found to be ~30 nM (FIG. 5), consistent with those for CT binding to GD1b (Fang, Y., Frutos, A. G., and Lahiri, J. "Ganglioside microarrays for toxin detection", Langmuir, 2003, 19, 1500-1505). Most interestingly, the indirect competitive binding of the universal readout (i.e., Cy3-avidin) and toxin only happened in the center of the microspot comprising both biotin-DHPE and GD1b, in which the size of center part is same as the pin used for printing. It is believed that this event is mainly due to the lipid raft formation of ganglioside lipids. It is known that small ganglioside-rich microdomains (lipid rafts) can exist within larger ordered domains in both natural and model membranes (Mandala, S. M., Thornton, R., Tu, Z., Kurtz, M. B., Nickels, J., Broach, J., Menzeleev, R., and Spiegel, S. (1998) *Proc. Natl. Acad. Sci. U.S.A.* 95, 150-155). During the printing a small volume of lipid mixture is deposited in each microspots, and lipid vesicles tend to rapture and spread in the each microspots. Lipid rafts rich in gangliosides, however, tend to stay in the contact area due to low fluidity, while lipids having a poor concentration of gangliosides tend to spread more easily than the other lipid rafts. These features lead to the formation of a microspot in which there are certain ganglioside-rich-domains in the center and ganglioside-poor domains far from the center. Biotin-X-DHPE, however, tends to uniform distribute across the dimension of each microspots. Thus, toxin can bind to the ganglioside-rich domains, and thereby more efficiently compete with Cy3-avidin binding.

The present invention has been described in general and in detail by way of examples. Persons skilled in the art understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

I claim:

1. A method for determining relative orientation of biological molecules on a microarray, the method comprising:

providing a substrate having biological molecules associated with a biological membrane deposited and arrayed in a number of microspots;

providing a control spot containing a common lipid associated ligand as in all other said microspots on said substrate;

providing a solution containing a labeled receptor having a binding affinity for said common lipid associated ligand;

performing an indirect competition assay in which said receptor binds with said lipid associated ligand and competes with a target of interest specific for the biological molecules;

measuring and comparing a relative signal intensity from said control spot with a relative signal intensity from all other said microspots; and assessing the orientation of the biological molecules using steric hindrance due to the indirect competition assay.

2. A method for assessing quality control of biological microarray performance, the method comprises:

providing a substrate with biological membrane probes immobilized in a number of microspots and having a common lipid associated ligand associated with said probes;

providing a labeled universal readout unit with an affinity for binding with said common lipid associated ligand;

performing an indirect competition assay be reacting the universal readout units with the biological membrane probes on the substrate, such that the universal readout units bind to the common lipid associated ligands and competes with a target of interest specific for the biological membrane probes;

monitoring a relative signal intensity from said labeled universal readout unit; and assessing the orientation of the biological molecules using steric hindrance due to the indirect competition assay.

3. The method according to claim 2, wherein said microarray incorporates a control spot constituted of a mat of said common lipid associated ligand alone.

4. The method according to claim 2, wherein said monitoring a relative signal intensity comprises assessing relative orientation of immobilized biological molecules embedded in lipid bilayers by measuring and comparing the relative signal intensity from a control spot with the relative signal intensity from all other said microspots.

5. The method according to claim 2, wherein said monitoring a relative signal intensity comprises assessing spot morphology of the array by measuring and comparing the relative signal intensity and distribution from a control spot with the relative signal intensity from all other said microspots.

* * * * *